(12) United States Patent
Guaragno

(10) Patent No.: US 8,882,503 B2
(45) Date of Patent: Nov. 11, 2014

(54) FOOT PEDAL CONTROLLER FOR DENTAL SCALER

(75) Inventor: Kenneth R. Guaragno, Spring Grove, PA (US)

(73) Assignee: Dentsply International, Inc., York, PA (US)

( * ) Notice: Subject to any disclaimer, the term of this patent is extended or adjusted under 35 U.S.C. 154(b) by 159 days.

(21) Appl. No.: 13/479,801

(22) Filed: May 24, 2012

(65) Prior Publication Data

US 2012/0301844 A1 Nov. 29, 2012

Related U.S. Application Data

(60) Provisional application No. 61/490,354, filed on May 26, 2011.

(51) Int. Cl.
*A61C 1/02* (2006.01)
*A61C 1/00* (2006.01)
*A61C 17/20* (2006.01)

(52) U.S. Cl.
CPC ............... *A61C 1/0023* (2013.01); *A61C 17/20* (2013.01)
USPC ........................................................ 433/101

(58) Field of Classification Search
CPC ................................................... A61C 1/0023
USPC .................... 433/97–101; 307/112, 116, 119, 307/139–143; 246/16; 200/86.5; 74/481, 74/512–514, 560
See application file for complete search history.

(56) References Cited

U.S. PATENT DOCUMENTS

| | | | |
|---|---|---|---|
| 3,526,036 A | 9/1970 | Goof | |
| 4,051,337 A | 9/1977 | Warrin | |
| 4,205,236 A | 5/1980 | Goof | |
| 5,386,600 A | 2/1995 | Gilbert, Sr. | |
| 7,488,173 B2 | 2/2009 | Bochi | |
| 7,625,208 B2 | 12/2009 | Warner | |
| 2005/0043828 A1* | 2/2005 | Tanaka et al. | ................... 700/83 |
| 2007/0166661 A1 | 7/2007 | Brenner et al. | |
| 2007/0166662 A1* | 7/2007 | Lint et al. | ...................... 433/101 |
| 2008/0166685 A1 | 7/2008 | Rosenblood et al. | |
| 2009/0087813 A1 | 4/2009 | Cai et al. | |

FOREIGN PATENT DOCUMENTS

| | | |
|---|---|---|
| DE | 202005005530 U1 | 8/2006 |
| EP | 1811264 A1 | 7/2007 |
| EP | 2062547 A1 | 5/2009 |
| WO | 9801736 A1 | 1/1998 |

* cited by examiner

*Primary Examiner* — Heidi M Eide
*Assistant Examiner* — Matthew Saunders
(74) *Attorney, Agent, or Firm* — McNees Wallace & Nurick LLC

(57) ABSTRACT

A method for controlling a dental instrument includes a foot pedal responsive to commands from a user. An operating mode is selectable between normal and boost cycle. A conventional mode is selectable by pressing and holding the foot pedal to a first level to operate in normal mode. The foot pedal operates in a boost mode when the pedal advances to a second level. Maintained mode is selectable by tapping the foot pedal to change modes between idle, normal and boost mode. Each mode is switched by tapping the foot pedal. The pedal switches between the second process and the first process by pressing and holding the foot pedal at the desired level corresponding to normal or boost mode. The pedal switches from the first process to the second process by tapping the foot pedal at the level corresponding to normal or boost.

7 Claims, 14 Drawing Sheets

Turning-on ultrasonics:

*State:* foot pedal asleep, u/s is disabled, and switch one and two are high

1. Momentarily closing swiotch one (Literally tap the pedal)
   a) Switch one will transition from high-to-low-to-high greater than 100 msec and less than 1 second.
   GO TO - u/s enable (if insert is in handpiece, if ignore latch-on command)
1. Momentarily closing switch one and two (Literally tap pedal)
   a) Both switch one and two transition from high-to-low-to-high greater than 100 msec and less than 1 second.
   GO TO - u/s enable (if insert is in handpiece, if not ignore latch-on command).

*State:* Latched-in normal mode with u/s enabled, switch one is high (after 5 minutes of no foot pedal activity time out. Go to Off).

*Note 1: This time out could be replaced later with handpiece usage monitoring.*
*Note 2: Further safety feature, after 30 seconds of operation if water flow is not detected u/s should be disabled.*

FIG. 1A

Turning-off ultrasonics:

*State:* foot pedal awake and transmitting, (u/s is enabled or u/s in boost-mode is enabled), and switch one and two are high.

1. Close switch one. Literally tap the pedal.
   a) Switch one will transition from high-to-low-to-high greater than 50 msec (note: 50 msec might be needed to ignore switch bounce).
   OR
2. Close switch one and two. Literally tap the pedal.
   a) Both Switch one and two transition from high-to-low-to-high greater than 50 msec (note: 50 msec might be needed to ignore switch bounce).
   OR
3. Close switch one. Press and Hold.
   1. Switch one trasitions from high-to-low and is held down. Once switch one is released GO TO - u/s disabled.
4. If switch one and two are held low boost should work and u/s should stay enabled if switch one and two are released simultaneously (within 150 msec).... keep u/s enabled.
5. If switch one and two are held low boost should work, if switch two is released and then switch one is used held for more than 1 second and then released .... Go To ----u/s disabled.

FIG. 1B

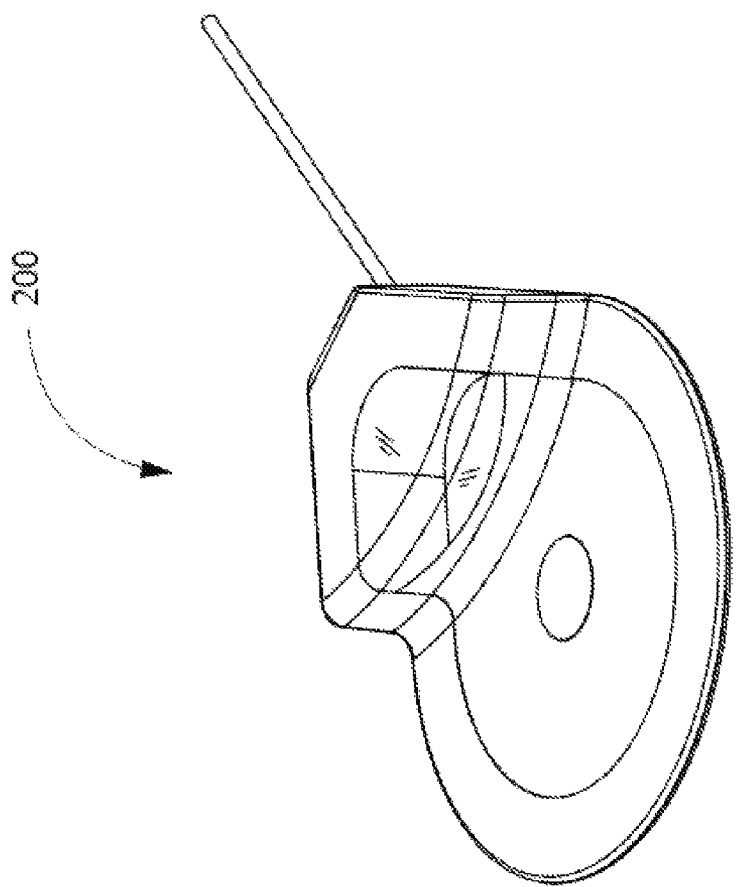

FOOT PEDAL CONTROLLER FOR DENTAL SCALER

CROSS-REFERENCE TO RELATED APPLICATIONS

This application claims priority from and the benefit of U.S. Provisional Patent Application No. 61/490,354, filed May 26, 2011, entitled "FOOT PEDAL CONTROLLER FOR DENTAL SCALER", which is hereby incorporated by reference.

BACKGROUND

The application generally relates to dental ultrasonic scalers and similar dental instruments. The application relates more specifically to a foot pedal controller for a dental scaler.

Dental professionals may be required to use a foot pedal or foot switch to enable an ultrasonic scaler for removing plaque and calculus from teeth. During the course of a single day the dental professional may treat up to a dozen patients, each patient requiring several minutes of ultrasonic scaling. Mechanical foot pedals for ultrasonic scalers may include a spring return that opposes the force applied by the foot when operating the foot pedal. The spring force must be sufficient to overcome any friction in the foot pedal to prevent accidental turn-on of the scaler. Dental hygienists may suffer from foot, leg, and back pain, due to strain associated with foot control operation.

There is a need for a foot pedal that enables the user by a single action or event to enable ultrasonic activity, and by a singular event to de-activate ultrasonic activity, for example, by simply touching a foot pedal. The singular event enables ultrasonics so that it operates continuously at a pre-set power level without requiring the user to maintain pressure or force on the foot pedal.

Further, there is a need for a dental scaler system to provide an indicator that there is "no water pressure". If the ultrasonic power is applied and the dental scaler unintentionally latched in the on state with an insert in the handpiece, while the cooling water supply is turned off, the insert tip and handpiece may become overheated. It is undesirable for the clinician to handle a hot handpiece or touch a hot insert.

Intended advantages of the disclosed systems and/or methods satisfy one or more of these needs or provide other advantageous features. Other features and advantages will be made apparent from the present specification. The teachings disclosed extend to those embodiments that fall within the scope of the claims, regardless of whether they accomplish one or more of the aforementioned needs.

SUMMARY

The disclosure relates generally to a foot control device for an ultrasonic dental scaler. The dental scaler may be activated by applying a momentary tapping force to the foot pedal control device, which latches the foot pedal control device in one of at least two control states. By latching the foot pedal control device in a control state, the need for the dental professional, or clinician, to maintain pressure on the foot pedal control device with his or her foot is eliminated. The foot pedal control device may include a standard mechanical foot control with software based latching feature. Alternately, a low profile floor pad with the ability to detect the presence of the clinician's foot using proximity sensors, e.g., capacitive touch, light beam technology.

In one embodiment, a method is disclosed for controlling a dental instrument. The method includes providing a foot pedal and a control circuit for communicating control signals from the foot pedal to the dental instrument, wherein the foot pedal is responsive to commands communicated by a user applying a force to the foot pedal; selecting between a first operating mode for ultrasonic operation of the dental instrument, and a second operating mode for ultrasonic operation of the dental instrument using the foot pedal. Selecting the first operating mode includes applying a sustained force to the foot pedal to a first level to actuate at least one switch on the foot pedal; the foot pedal configured to operate the dental instrument in the first operating mode in response to the sustained force being applied to the foot pedal; and selecting the second operating mode includes applying a momentary force to the foot pedal to transition from the first operating mode. Transitioning from the second operating mode to the first operating mode is accomplished by applying a momentary force to the foot pedal; and transitioning from the first operating mode to the second operating mode is accomplished by applying a momentary force to the foot pedal.

In another embodiment a control system is disclosed for controlling a dental instrument by a user's foot. The control system includes a foot pedal and a control circuit for communicating control signals from the foot pedal to the dental instrument. The foot pedal includes at least two switches. The switches are operable in response to a force applied to the foot pedal. The foot pedal is arranged to select between a first operating mode and a second operating mode for ultrasonic operation of the dental instrument using the foot pedal. The control circuit is arranged to select the first operating mode in response to a sustained force applied to the foot pedal to move the foot pedal to a first level to actuate at least one switch on the foot pedal; and to select the second operating mode in response to a momentary force applied to the foot pedal to move the foot pedal to the first level.

In yet another embodiment a foot pedal control for a medical instrument is disclosed. The foot pedal includes a communication link for communicating control signals to the medical instrument. The foot pedal includes software for detecting and distinguishing a sustained force application and a momentary force application. The foot pedal control is programmed to operate in a first operating mode in response to a sustained force application, and to operate in a second operating mode in response to a momentary force application.

Certain advantages of the embodiments described herein include a foot pedal that has both normal and boost functionality along with software implemented touch-type latching feature.

Alternative exemplary embodiments relate to other features and combinations of features as may be generally recited in the claims.

BRIEF DESCRIPTION OF THE FIGURES

FIG. 1A is a diagram of exemplary control logic for turning on ultrasonics with the latching foot pedal.

FIG. 1B is a diagram of exemplary control logic for turning off ultrasonics with the latching foot pedal.

FIGS. 7, 7A and 7B illustrate exemplary foot pedal controllers.

DETAILED DESCRIPTION OF THE EXEMPLARY EMBODIMENTS

Figure 1:
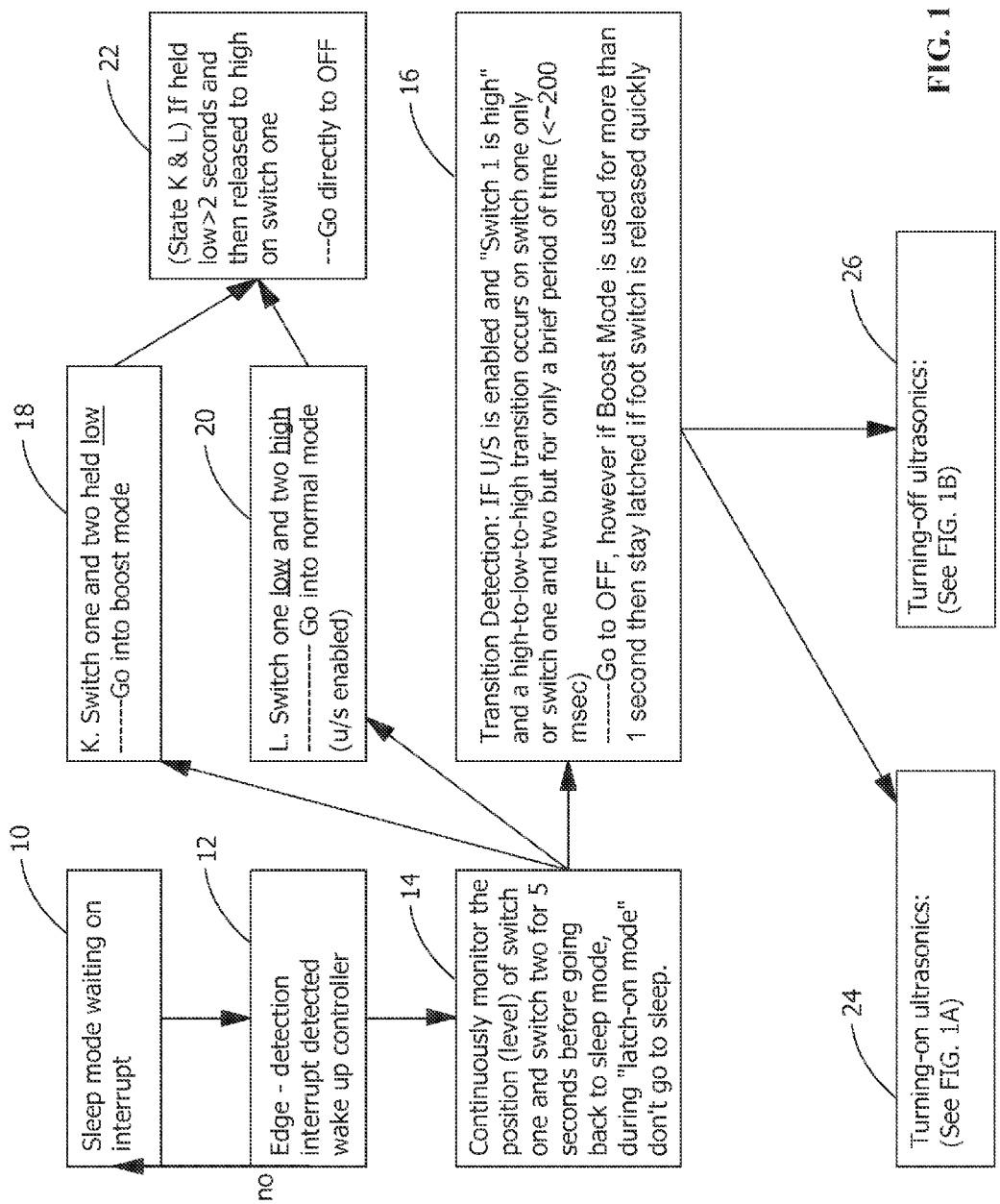
FIG. 1 is a diagram of exemplary control logic for a latching foot pedal.

Referring to FIG. 1, a diagram of a control logic scheme is shown for latching a foot pedal 200 with a boost-mode, and for providing two-stage functionality in a foot pedal 200 controller for a dental scaler (not shown). In one embodiment, the control logic may be implemented in software. While it is preferred that the control algorithm be embodied in a computer program(s) and executed by a microprocessor, it is to be understood that the control algorithm may be implemented and executed using digital and/or analog hardware by those skilled in the art. An exemplary foot pedal for a dental scaler is described in U.S. patent application Ser. No. 13/084,896, filed Apr. 12, 2011, entitled System Including a Wireless Dental Instrument and Universal Wireless Foot Controller by Lint, et al. An exemplary dental scaler instrument is described in U.S. patent application Ser. No. 13/084,945, filed Apr. 12, 2011, entitled Method of Selectively Pairing Wireless Controller to Multiple Dental/Medical Instruments by Lint, et al., both of which patent applications are incorporated herein by reference.

At a first state indicated by reference numeral 10, e.g., after an extended period of inactivity of the dental scaler, the latching foot pedal 200 is in a sleep mode. In sleep mode, foot pedal 200 does not send out any signals to dental scaler. Foot pedal 200 continuously monitors the circuit for an interrupt signal and remains in sleep mode while waiting to receive an interrupt signal. Upon receiving an interrupt signal, e.g., an edge-detect interrupt, foot pedal 200 wakens, at state 12, and proceeds to continuously monitor the level or position of switches one and two at state 14.

Figure 4:
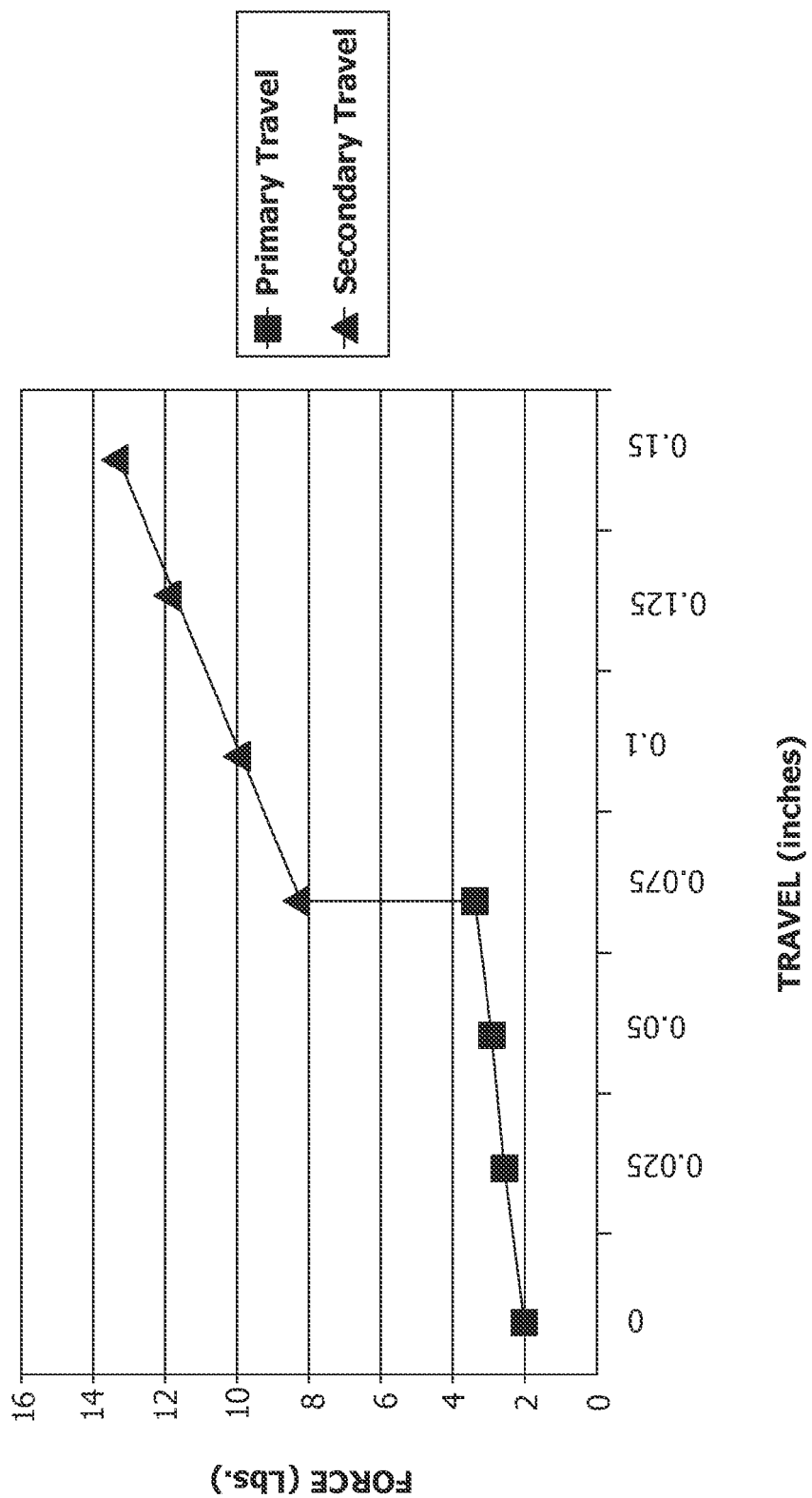
FIG. 4 is a graphical representation of applied force versus travel distance of an actuator for an exemplary foot pedal.

The foot pedal 200 has two switches. Normally switch one and switch two operate at a high logic voltage level (3 Volts). When foot pedal 200 is depressed switches one and two close, pulling their logic lines to ground and activating the software that enables ultrasonic power at the scaler tip. Switch one closes before switch two. Switch one activates normal ultrasonic vibration of the ultrasonic tip 76 (FIG. 9) inserted in the scaler. Switch one activates ultrasonic vibration when depressed, i.e., a sustained force is applied by the user to an activating plunger to displace the foot pedal 200 within the primary travel range of the foot pedal 200, e.g., up to 0.075 inches (see, e.g., FIG. 4.). Switch two provides a boost mode for ultrasonic tip operation that is activated within the secondary range of travel of the pedal, e.g., from 0.075 inches to about 0.15 inches of displacement or travel. Boost mode provides a temporary increase in ultrasonic scaling power for quick removal of tenacious calculus without touching the unit. Boost mode remains as long as the clinician has the foot pedal pressed all the way down. Boost mode may be used intermittently as required.

At state 14, control logic monitors the position of switch one and switch two for a predetermined interval, e.g., 5 seconds. If no signal is received within the predetermined interval, foot pedal 200 returns to sleep mode, unless the foot pedal 200 control logic is in latch mode. If foot pedal 200 control logic is in latch mode, then foot pedal 200 does not return to sleep mode.

From state 14, if control logic detects transition at state 16, i.e., if a microswitch power is enabled and switch 1 is high, and a high to low to high transition is sensed on switch one only, or on both switches one and two but for a short duration, e.g., less than 200 microseconds, then the system is turned off. However, if at step 16 boost mode is used for more than 1 second then the control logic stays latched in normal mode if the foot pedal 200 is released quickly. Note that at state 18, when switch one and switch two are both held low, the control logic to the scaler enters boost mode. At state 20, when switch one is held low and switch two is high, the microswitch is enabled and the control logic activates normal operating mode for the dental scaler. Also, at state 22, in states 18 and 20, if held low greater than, e.g., two seconds, and then released to high on switch one, then the system, the switch changes states creating a pulse of which may be, e.g., in the range of >0.100 and <1.

From state 16, transition detection may also be applied to turn on ultrasonic vibration in the dental scaler, at state 24, or to turn off ultrasonic vibration of the dental scaler at state 26. At state 24, with the foot pedal 200 in sleep mode, and switch one and two are high, momentarily closing switch one, i.e., by the operator tapping its foot on foot pedal 200, switch one will transition from high-to-low-to high greater than 100 msec and less than one second. The control logic then enables microswitch power, provided an insert is properly inserted into the dental scaler. If no insert is present, the control logic ignores the latch on command indicated by the tapping motion of the operator. If momentarily closing both switch one and switch two, e.g., by tapping the pedal, both switch one and switch two transition from high to low to high greater than 100 msec and less than one second. Again, the control logic then enables the microswitch, provided an insert is properly inserted into the dental scaler. If no insert is present, the control logic ignores the latch on command indicated by the tapping motion of the operator.

Further, if the system is latched in normal operating mode with the microswitch power enabled, and switch one is high after a predetermined time-out period, e.g., five minutes, in which there has been no activity with respect to the foot pedal 200, then the control logic switches the microswitch power to the off position.

At step 26, the sequence for turning off the ultrasonic vibration of the scaler begins with the foot pedal 200 in a wakened state and transmitting, i.e., the microswitch power is enabled or the microswitch power in boost mode is enabled, and switch one and switch two are both high. In one embodiment, the operator may turn off the ultrasonic vibration of the scaler by closing switch one, e.g., by tapping its foot on the foot pedal 200, so that switch one transitions from high to low to high for a predetermined interval, e.g., greater than 50 msec, so that the system will ignore switch bounce. In another embodiment, the operator may close switch one and switch two, e.g., by tapping on the foot pedal 200, such that switch one and switch two transition from high to low to high for a predetermined interval, e.g., greater than 50 msec, so that the system will ignore switch bounce and any inadvertent switch closure that may occur as a result of kicking, moving or bumping the foot pedal. In still another exemplary embodiment, the operator may close switch one and maintain switch one closed, e.g., by pressing and holding the switch, causing switch one to transition from high to low and maintained in the low state until released. Once released the microswitch power is disabled. In another exemplary embodiment, the operator may keep switch one and switch two held low, so that the ultrasonic scaler will operate in boost mode and the microswitch power will remain enabled. If switch one and switch two are released approximately simultaneously, e.g., within 150 microseconds of one another, then the microswitch will remain enabled. In one more embodiment, switch one and switch two are held low and the ultrasonic scaler will operate in boost mode and the microswitch power will remain enabled. If switch two is released and then switch one is held for more than one second and then released, then the microswitch power is disabled. Note that microswitch power, as used herein, indicates that the ultrasonic system is powered or energized.

Figure 2:
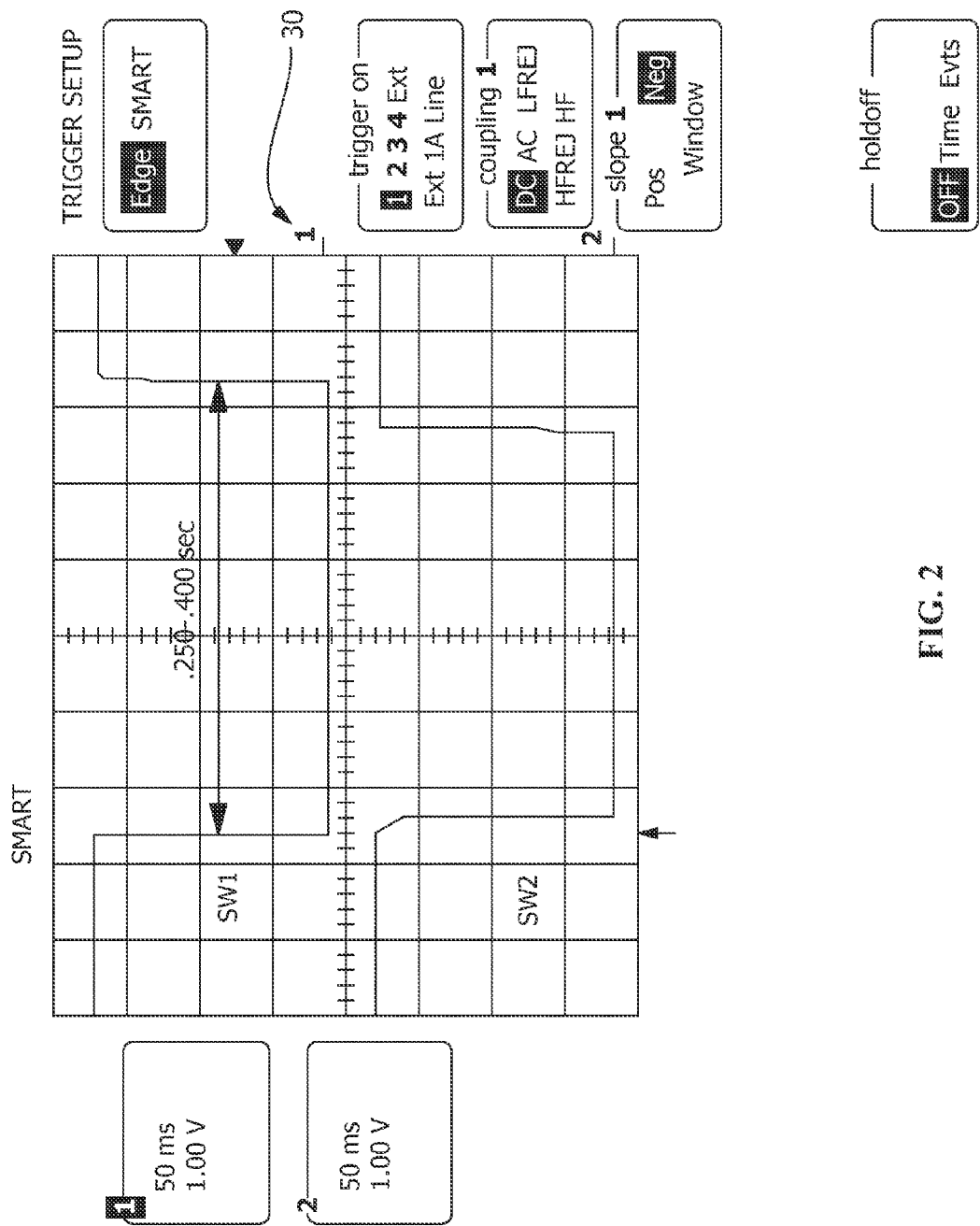
FIG. 2 illustrates the state of switches during a momentary tapping to signal a change of control state of a dental scaler.

The latching feature maintains the ultrasonic action of a dental scaler in an on state without the need for the operator to continuously hold the switch in the on position. Foot pedal 200 may provide a boost mode that enables the dental scaler to be latched in the ON state. When, for example, a user, e.g., a dental hygienist, depresses the pedal into boost mode and quickly releases foot pedal 200 the software protocol causes the dental scaler to remain latched in the ON state. A slow release or use of the pedal in normal mode for any length of time will de-latch the pedal so that when the hygienist lifts her foot fully the pedal unit turns off. Additionally if the dental hygienist were to depress the pedal for more than one second, it would work in a classic-mode providing normal operation and normal boost functionality. Specifically, the foot pedal 200 will activate and de-activate the ultrasonic scaler instantly, bypass the latch-on mode through software. FIG. 2 below illustrates an edge trigger 30. The edge trigger 30 demonstrates a typical switch closure that occurs when the foot pedal 200 is momentarily activated by tapping with the foot. The detection of a brief switch closure enables the control logic to differentiate between a foot pedal 200 being tapped and a foot pedal 200 being depressed.

In an alternate embodiment, a push button switch (not shown) may be included, e.g., on the handpiece. The button will allow a user to disable the latch-on feature. Disabling the latch feature might be advantageous for special needs patients that might sit up unexpectedly, and leaving insufficient time for the hygienist to tap the foot pedal. If the push button switch has been disabled the hygienist may just lift her foot immediately to power off the hand piece.

The control logic may provide a timeout circuit so that after a predetermined time interval, for example 5 minutes, the dental scaler would turn off ultrasonic vibration of the dental scaler, and fluid flow through the dental scaler. In the event the foot pedal 200 is accidentally or unintentionally activated, the control logic may disable the latching feature when it senses that an ultrasonic insert is not present in the dental scaler handpiece, to prevent leakage of cooling fluid from the handpiece. In another embodiment a flow sensor may be incorporated in the water line as a safety feature; if an insert is in the handpiece and the cooling water is turned off the touch n-go feature can be disabled.

A water flow sensor may also be employed to provide self diagnostics and an added safety feature needed for the latching pedal. A water flow sensor may provide a positive indication that cooling water is flowing through the dental scaler. Cooling water supply to the dental scaler or handpiece may be interrupted for multiple reasons, e.g., the flow control could be turned off during wipe disinfection, the dedicated water reservoir for the dental scaler may be empty or not pressurized, the dental scaler could be clogged or malfunctioning, or the water supply to the dental scaler could simply be shut off or disconnected.

Figure 9:
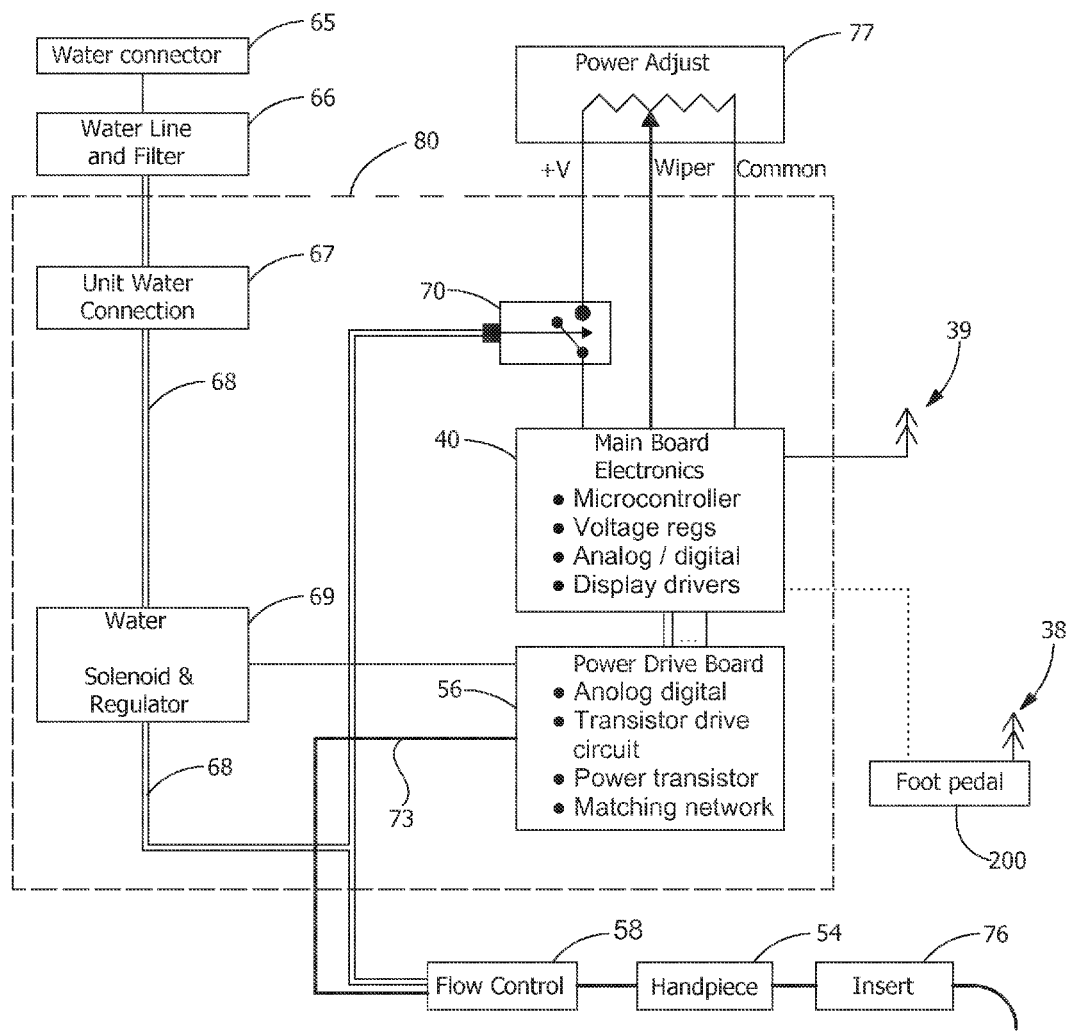
FIG. 9 is a schematic diagram of a water pressure monitoring circuit.
Figure 10:
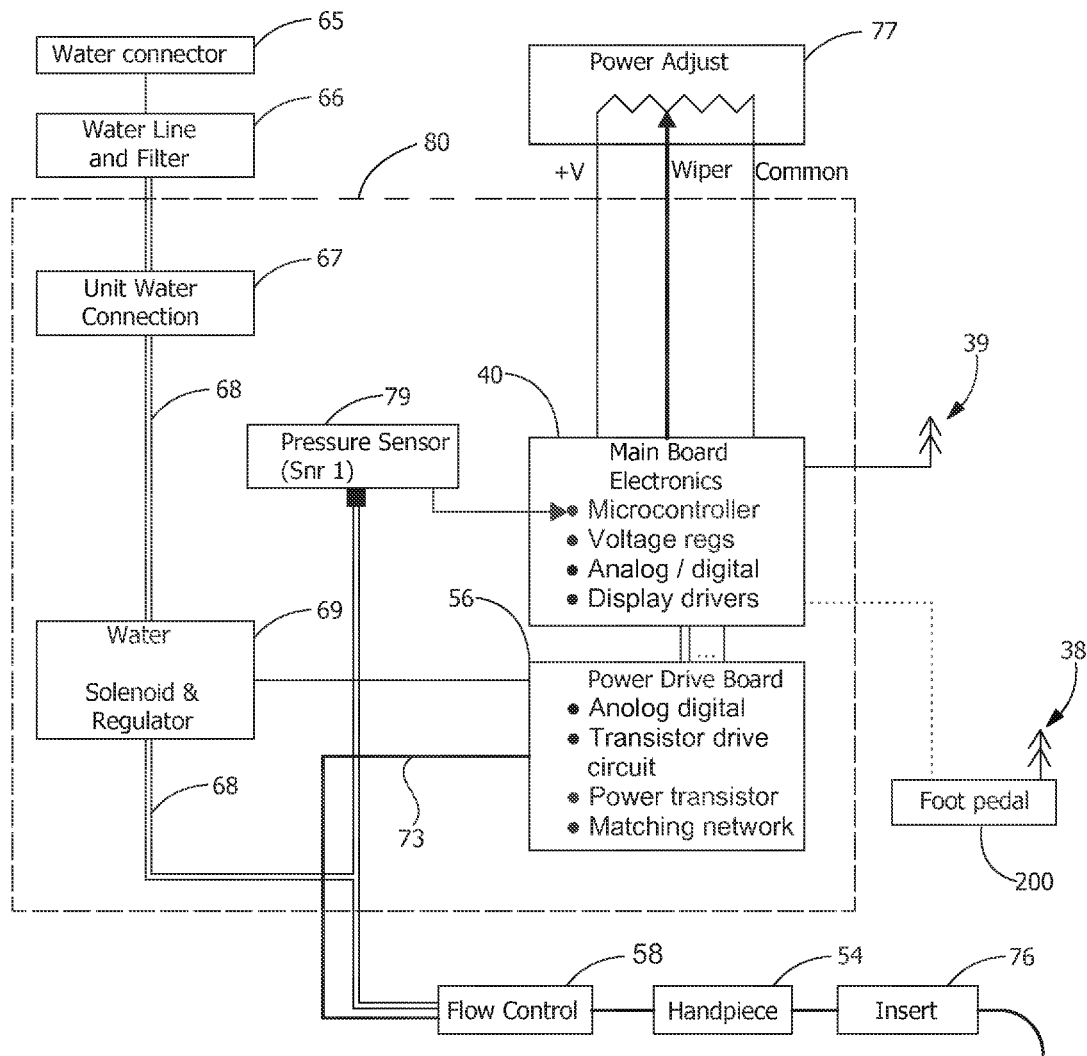
FIG. 10 is a schematic diagram of an alternate embodiment of a water pressure monitoring circuit.
Figure 11:
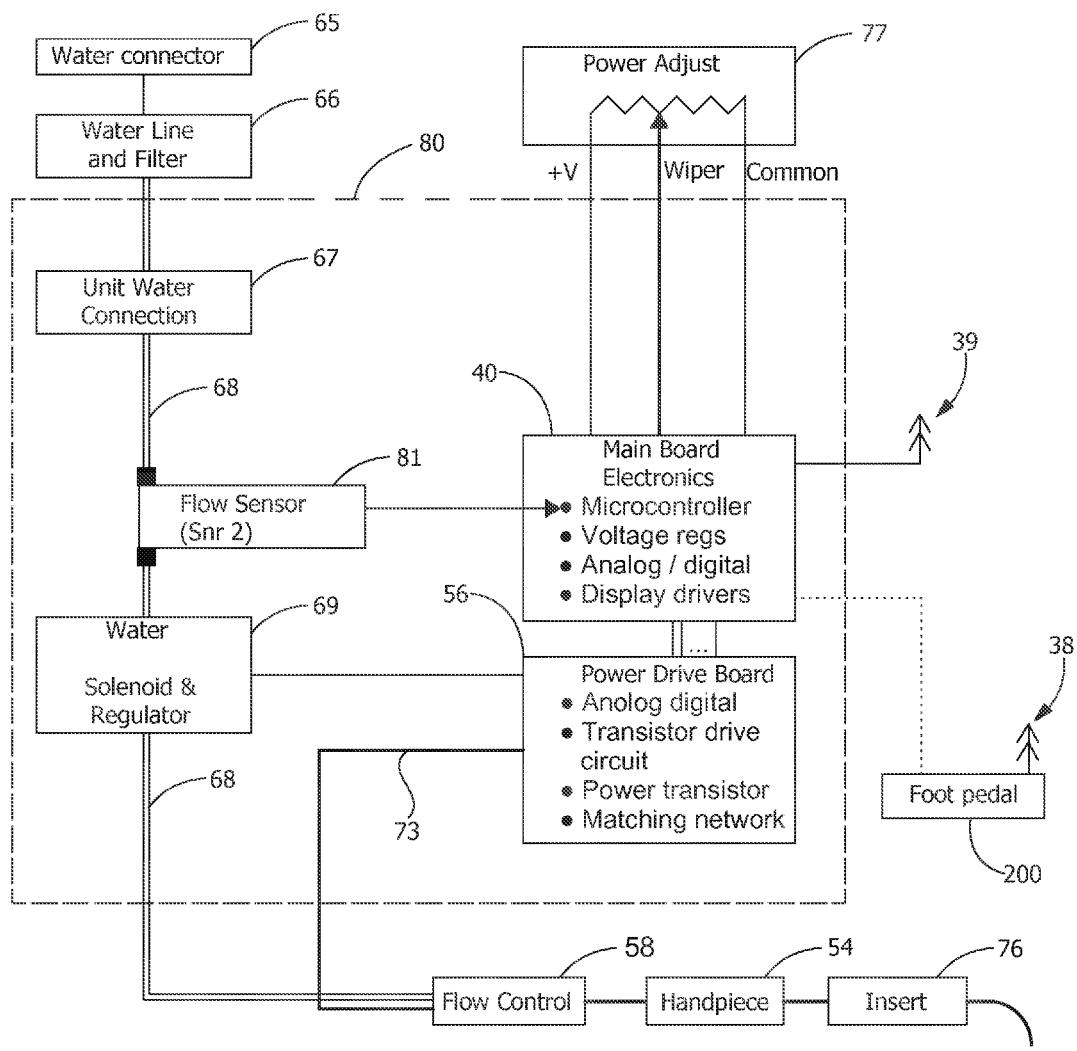
FIG. 11 is a schematic diagram of another alternate embodiment of a water pressure monitoring circuit.

Referring to FIGS. 9-11, cooling water is supplied to a control unit 80 via connector 65 attached to a water line and filter 66. Water line and filter 66 are in fluid communication through a water line with an internally positioned water connection 67 inside control unit 80. Through water connection 67 water flow is controlled by a solenoid and regulator device 69. Solenoid and regulator device 69 are in electrical communication with a power drive board 56. Power drive board 56 is configured to convert analog signals to digital signal to communicate with a main microcontroller board 40. Power drive board 56 includes transistor drive circuits for power transistors and a matching network to control operation of solenoid and regulator device 69, including opening and closing the solenoid to provide water flow and regulating the flow in water line 68. A pressure switch 70, pressure sensor 79 or flow sensor 81 may be provided in fluid communication with water line 68 for monitoring water parameters to ensure available supply of cooling water to handpiece 54. The various sensor configurations are described below with respect to FIGS. 9-11.

Referring to FIG. 9, in a first embodiment, a pressure switch 70 may be used to monitor water pressure. Pressure switch 70 is configured to close a set of electrical contacts when a preset pressure is applied by the fluid in the line. For example, pressure switch 70 may be set to open the electrical contacts below a predetermined low pressure threshold, e.g., a minimum head pressure as low as 4 pounds per square inch (psi), or in another embodiment a minimum head pressure as low as 15 psi, and close the electrical contacts above predetermined low pressure threshold, e.g., 4 psi-15 psi, and thus monitor fluid pressure in the tubing 68 connected to the handpiece. When the pressure drops below the low pressure threshold, scaler or handpiece 54 may be configured to respond in a variety of ways, e.g., by shutting down, preventing, or limiting the ultrasonic power be sent to the handpiece. In one embodiment, a sensed low pressure would permit the start-up of the ultrasonic insert and would integrate the pressure switch contacts into the scaler power level control circuit 72. The scaler power level control circuit would not completely cut of power to the ultrasonic circuit, but would limit the output power from the scaler power level control circuit to a low level such that cooling fluid is not required to prevent the generation of heat does not exist.

Referring next to FIG. 10, in another embodiment a safety circuit may be provided to prevent the generation of heat in the tip 76 and handpiece if adequate lavage is not available. Referring to FIG. 10 a schematic diagram of a water pressure monitoring circuit includes a pressure sensor 79 disposed in water path 68 to monitor fluid pressure. The output signal from pressure sensor 79 may then be input to an analog-to-digital converter on main board 40. A microprocessor on main controller board 40 can then compare the converted signal from the A-D converter with a predetermined pressure threshold or range. The control circuit 48 can then determine if the state of the system requires lavage. When ultrasonic power is disabled and during the first 100 milliseconds of ultrasonic start-up the pressure sensor signal will be low or in transition and therefore can be ignored by the microcontroller.

Referring next to FIG. 11, in another embodiment a flow sensor 81 is placed in the flow path of water line 68 to indicate the presence of cooling water availability in control unit 80, e.g., water is present and flowing. Flow sensor 81 is in electronic communication with main microcontroller board 40. Flow sensor may be configured to detect a single fault condition, e.g., loss of water supply, solenoid failure, water leak, or clogged water line. Flow sensor 81 transmits an electronic signal to the microcontroller. The flow sensor signal may be analog or digital depending on the type of flow sensor. The microcontroller in main microcontroller board 40 is configured with software that monitors the sensor signal periodically and determines if water flow is sufficient to assure cooling water for the handpiece power level setting and operating time of the insert. Water flow could be ignored at startup through a simple software start-up routine and self diagnostics could be included to provide the end-user with more information about the status of their scaler. In addition a digital readout could display the flow rate on the units display. Displaying both power and water levels numerically will enable the clinician to record (i.e. patient records) preferred patient and instrument settings. This will help with patient comfort and reduce the time needed to setup the equipment. In one embodiment flow sensor may include a thermistor placed in the water line 68. A thermistor is an analog device which changes resistance value in response to temperature change. The thermistor will exhibit a rapid change in resistivity if no water is present in the water path, a slow change in resistivity if water is present in the water path but not flowing, and no change or a reduction in resistivity when water is flowing. Preferably, the thermistor may have a small thermal capacitance.

Foot pedal 200 software may provide a unique automatic mode for a dental prophy system, e.g., a Cavitron Prophy Jet system manufactured by Dentsply Professional Inc., of York, Pa. Cleaning of teeth, including scaling and polishing, is sometimes referred to as prophylaxis or prophy. During the use of a prophy jet air polishing system the dental hygienist is instructed to work the pedal between its first and second stage. The conventional process of cycling the pedal every two seconds between rinse and jet air polishing can be replaced by a momentary tap activation of foot pedal 200. Once the system detects the presence of a prophy jet nozzle in the handpiece the dental scaler software is able to communicate with the foot pedal 200 so that the system and foot pedal 200 know to switch into an automatic jet polishing routine. The automatic jet polishing routine eliminates the need to pump the pedal every two seconds. The system may be programmed to switch automatically between rinse mode and jet polishing mode at alternating intervals, e.g., every 2 seconds. In one embodiment, the system may include short, medium and long cycle selection options for the alternating interval. E.g., a short interval cycle may be set at 1 second for jet polishing and ½ second for prophy rinse; a medium cycle may be set at 2 seconds polishing, and 1 second prophy rinse; and a long cycle may be set at 3 seconds polishing, 1 second prophy rinse. A selector switch may be provided on the handpiece to allow the user to select which of the short, medium or long cycles the user wishes to apply.

Figure 3:
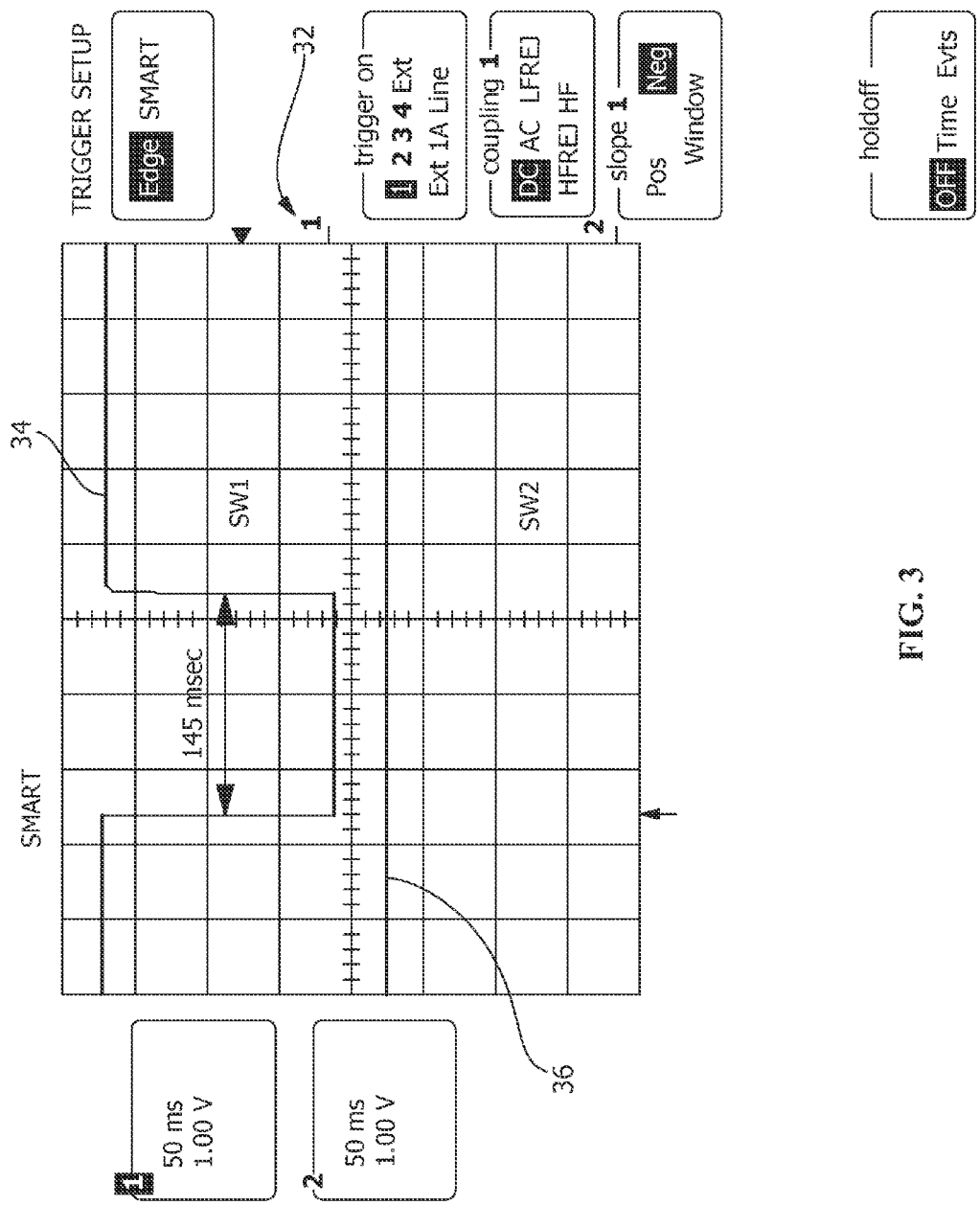
FIG. 3 is an exemplary profile of a switch bounce.

If the foot pedal 200 is kicked or accidentally bumped it might produce a brief switch closure as shown below. In one embodiment, the software may be programmed to ignore such a kick or bump as switch bounce. Referring to FIG. 3, an exemplary profile 32 of a switch bounce is shown on an oscilloscope trace 34. Trace 34 represents the state of switch one, from high to low to high. Switch two remains at a constant high state, as indicated by trace 36. When the switch bounce occurs, switch one transitions to the low state, and then returns to high, with the low state interval equal to 145 microseconds. The software can determine that the short duration, e.g., less than 150 microseconds, indicates that the signal was unintentional and the system does not generate a response to the switch bounce.

Figure 5:
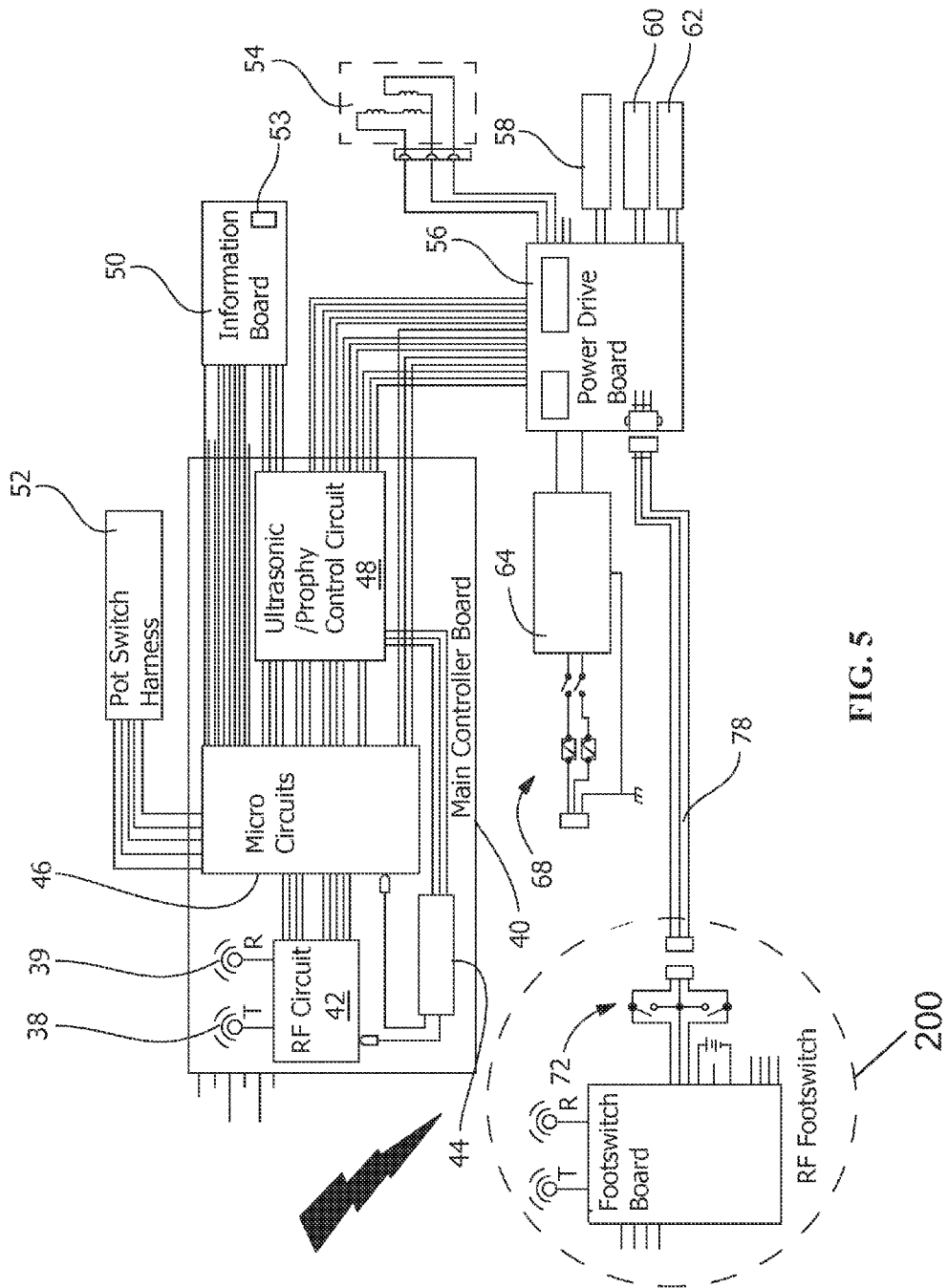
FIG. 5 illustrates an exemplary circuit diagram for a dental scaler controller with a wireless foot pedal control.

Referring next to FIG. 5, an exemplary circuit diagram for a dental scaler controller with a wireless foot pedal 200 control is shown. A main controller board 40 includes an RF circuit 42 with a transmit antenna 38 and a receive antenna 39 for communicating with an RF foot pedal 200. A voltage regulator circuit 44 provides power to RF circuit 42. A potentiometer switch on the operator panel (not shown) is connected to board 40 through a wire harness 52. Harness 52 is connected to micro circuits 46 that are in communication with an ultrasonic/prophy control circuit 48, and information board 50. Information board 50 may include a magnetic flux sensor 53 for sensing the presence of the handpiece in the cradle (not shown). Magnetic flux sensor 53 may include a conventional comparator circuit for a magnetic flux sensor.

A power drive board 56 is interconnected to ultrasonic/prophy control circuit 48 to power main controller board 40. Power drive board 56 also optionally drives microswitches when an auxiliary foot pedal 200 cable 78 is used to connect foot pedal 200 to power drive board 56, as discussed below. Power drive board 56 also drives auxiliary devices including water supply solenoid 58, which controls water flowing into the dental scaler or prophy device 54; a pinch valve 60 and an air bleed valve 62.

Figure 6:
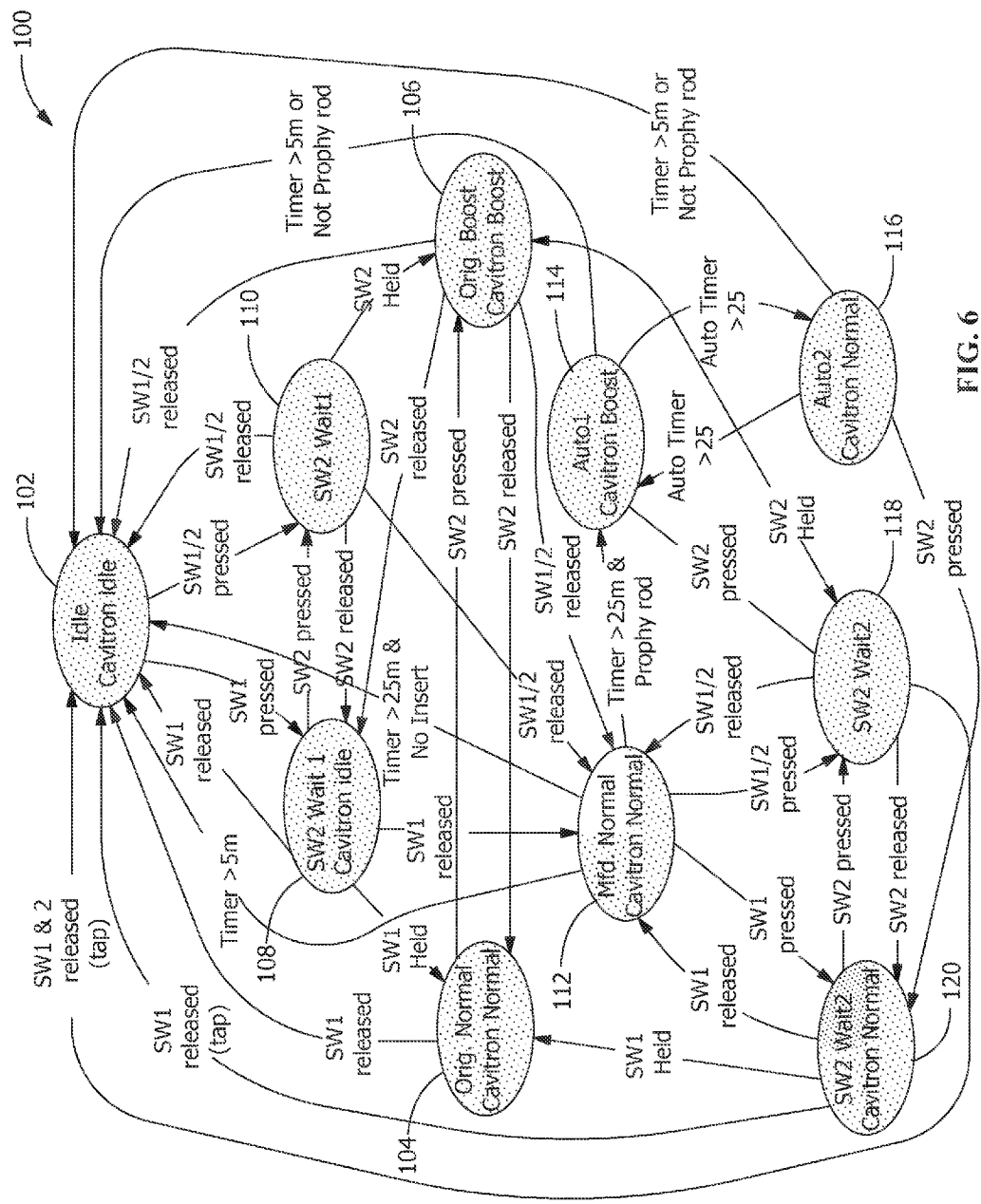
FIG. 6 illustrates an exemplary state-machine diagram for software logic for the foot pedal control.

Referring next to FIG. 6, one embodiment of a state-machine diagram 100 for software logic for the foot pedal 200 control is illustrated. The state machine diagram 100 corresponds generally with the control logic of FIG. 1. Conventional operating modes for an ultrasonic dental scaler include an idle mode 102, a scaler original or normal operating mode 104, and a scaler boost operating mode 106. Previous ultrasonic dental scalers employed a two-level switch to switch from idle mode to normal mode when a first switch was depressed, and to boost mode when the first switch and a second switch were depressed. Releasing either or both of the first and second switches returned the ultrasonic dental scaler to its prior mode. The state-machine diagram 100 includes additional modes as described below, which allows the operator the option to control the ultrasonic dental scaler with the foot pedal 200 in the way that conventional foot pedals have been operated to control dental scalers, or in a new control scheme referred to as tap on/tap off mode. It should be noted that first switch and second switch may be, e.g., a pair of microswitches that are both actuated by a single pedal, wherein the length of displacement or travel of the pedal determines whether one or both of the first and second switches closes.

When in idle mode 102, the operator may press first switch of the foot pedal 200 to advance to a first switch first wait mode 108. If first switch is held for more than a predetermined wait interval, e.g., one second, the software logic proceeds to normal operating mode 104. If however, before the second switch is activated before the predetermined interval, the control logic proceeds to a second switch first wait mode 110. Finally, if the first switch is released before either the expiration of the predetermined interval or activation of the second switch, the control logic proceeds to a maintained normal operating mode 112, which will be described in further detail below. In order to correct for inadvertent activation of the first switch, when in wait mode 108 first switch must remain closed for a threshold interval of at least, e.g., 0.25 seconds after the initial switch closure to be considered activated. Otherwise, the control logic effectively ignores the momentary switch closure and the control logic returns to idle mode 102. This threshold interval is commonly referred to as "debouncing" the switch, and is used to prevent activation resulting from persons accidently kicking or dropping items on the foot pedal 200.

Returning to mode 110, the second switch first wait mode 110 receives the second switch pressed signal from mode 108 following the first switch pressed signal. The waiting interval may be, e.g., one second. If while in mode 110 switch has already been released before the expiration of the predetermined interval, i.e., the control logic senses that the second switch was actuated by a tapping motion, rather than by being pressed and maintained, then the system proceeds to a maintained normal operation mode 112. The waiting interval at mode 110 is subject to debouncing as described above with respect to mode 108. In the maintained normal mode 112, the ultrasonic dental scaler is latched in the normal operation mode by the control logic, and the operator does not need to keep his or her foot on the pedal to keep the scaler operating.

From the maintained normal mode 112, a timer is set for a predetermined interval, e.g., five minutes, and if no activity is sensed from the foot pedal 200 before the five minute timeout interval, the control logic returns to idle mode 102. In another embodiment the timeout interval may be adjusted more or less to suit the operator preference or other suitable criteria. This is true for all predetermined intervals identified herein, which may be adjusted to account for actual operational conditions. The control logic may also return to idle mode 102 if at mode 112 no insert is detected in the handpiece, and the switch has been debounced. From mode 112, if a prophy rod is sensed in the handpiece, the control logic advances to an automatic boost mode 114 (also referred to as auto jet polishing mode), and begins an automatic cycle between automatic boost mode 114 and automatic normal mode 116 (also referred to as prophylaxis rinse mode), the automatic cycle continuing to switch between mode 114 and mode 116 at predetermined intervals until 1) a timeout period has passed without operator intervention or 2) second switch has been pressed to return the system to a wait mode 118 if pressed at automatic mode 114, or to wait mode 120 if pressed during automatic mode 116.

Other options available from mode 112 are to advance to a first switch second wait mode 120 when first switch is pressed, or to advance to a second switch second wait mode 118 when the second switch is pressed in sequence following the first switch being pressed, also, to advance to the second switch second wait mode 118 from the maintained normal mode 112, the operator can press first and second switch at the same time. Switch debouncing or ignoring short duration switch activations of one-quarter second or less applies to all of the state changes as indicated in FIG. 6. From either wait mode 118, 120, a tap on the foot pedal 200—indicated by first switch or both first and second switches being released before the expiration of the predetermined interval, e.g., two seconds—will return the control logic to idle mode 102. Alternatively, the system can switch between the wait modes 118, 120, by pressing the second switch (to advance from first switch second wait period 120 to second switch second wait period 118), or by releasing the second switch (to return to mode 120 from 118).

Yet another option is for the operator to advance the control logic from the maintained normal mode 112 back to the original normal operating mode 104, through one of the intermediate wait modes 120, 118, by pressing and holding down the foot pedal 200. Pressing and holding first switch always returns the system to normal operation mode 104, whether switching from the idle mode 102 to mode 104, or from the maintained normal mode 112. In both instances an intermediate wait mode 108 or 112, respectively) is interposed in order for the control logic to discriminate between a tapping action on the switch, and a press and maintain action on the switch.

If the system is in maintained normal mode 112, and both switches are pressed and held, then the control logic proceeds to original boost mode 106 via second switch second wait mode 118. In one embodiment, when normal mode 112 has been selected and a prophy rod is detected, after pressing and holding foot pedal 200 for two seconds a pulse of air will be generated to the handpiece 54, and after another period of two seconds that the foot pedal 200 is held down a second pulse of air will follow, to signal to the hygienist that the hand piece unit is about to enter automatic boost mode 114.

To summarize the state-machine diagram 100, the operator may choose to operate the normal and boost cycle in one of two processes. The first process is the conventional operation mode 104, 106 is accomplished by pressing and holding the foot pedal 200 to different levels to actuate one or both of its switches. The operator thus keeps his or her foot on the foot pedal 200 to stay in the normal or boost mode. The second process is that of a maintained or latching mode 112. The maintained mode is accomplished by tapping the foot pedal 200 to change states. In the second process, from idle mode 102, a tapping motion turns on and latches the ultrasonic dental scaler in normal mode 112, and a further tapping of second switch transitions the control logic to the original boost mode 106. From mode 106 when first and second switches are released after being held in the maintained normal mode 112, the control logic returns to the maintained normal mode 112. Thus the tapping motion relieves the operator of having to hold each switch in place during an entire procedure, and permits the operator to tap the foot pedal 200 and then position his foot in a comfortable position that is not fixed with respect to the foot pedal 200.

Further, at any point in an operation, the operator may press the foot pedal 200 to switch to the original operating normal mode or boost mode, and when in the original normal operating mode or boost mode, may tap the foot pedal 200 to switch to the maintained normal mode. In order to switch to original boost mode 106, both switches must be held down, however, although the control logic will return from boost mode 106 to the maintained normal mode 112 if that was the previous mode of operation.

Figure 7:
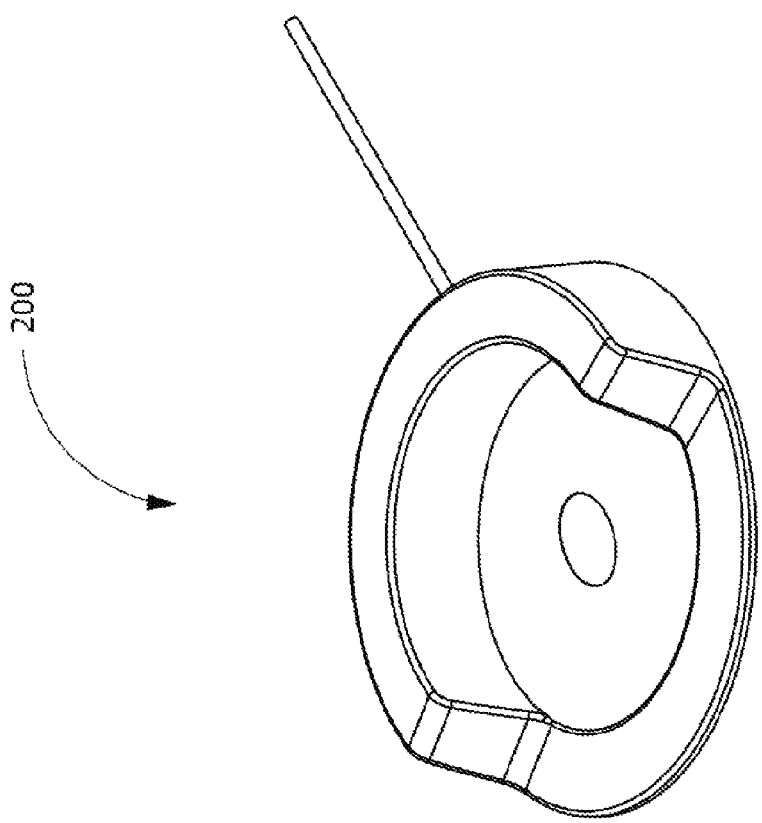

Referring next to FIG. 7, an exemplary ergonomic foot pedal 200 of the present invention is illustrated. An optical sensor or a capacitive touch pad 202 having a thin profile enhances the ergonomic benefits of the foot pedal. The operator's foot may be held in a neutral position, e.g., flat on the floor and operating would not require any significant downward pressure in order to operate the foot pedal.

In another aspect, force sensors (not shown) may be placed within the ergonomic foot pedal control to provide two activation modalities. In the first modality the proximity of the operator's foot is sensed, and in the second modality a force sensor detects a downward force. The embodiment of FIG. 7 provides both scaler activation and boost mode capability. FIG. 7A illustrates another embodiment of an ergonomic foot pedal 200. Foot pedal 200 may be configured as a wired controller or wireless controller.

Figure 7B:
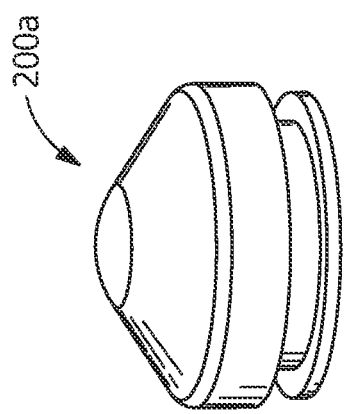
Figure 7C:
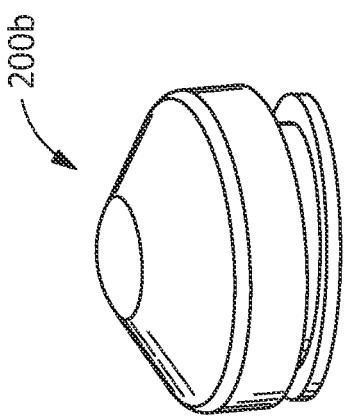
FIGS. 7C and 7D illustrate different states of the foot pedal controller shown in FIG. 7B.
Figure 7D:
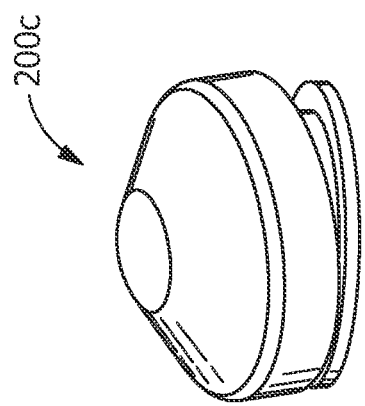

FIG. 7B illustrates yet another configuration for an exemplary foot pedal 200. With the foot pedal 200 of FIG. 7B, pressing anywhere on the top of the foot pedal controller activates the system. Three different states are shown, the first of which is foot pedal 200 in a non-depressed state 200a, a second state 200b in which foot pedal 200 is partially depressed in a first position, and a third state 200c in which foot pedal 200 is fully depressed in a second position—e.g., boost mode position.

In another embodiment the system may be programmed so that the foot pedal control does not stay latched in "boost" mode. Rather, the hygienist may hold down the pedal for boost mode, and if using the latching feature and select boost mode, the microswitch power stays latched-on when the hygienist lifts its foot off the pedal to disengage boost mode.

Figure 8:
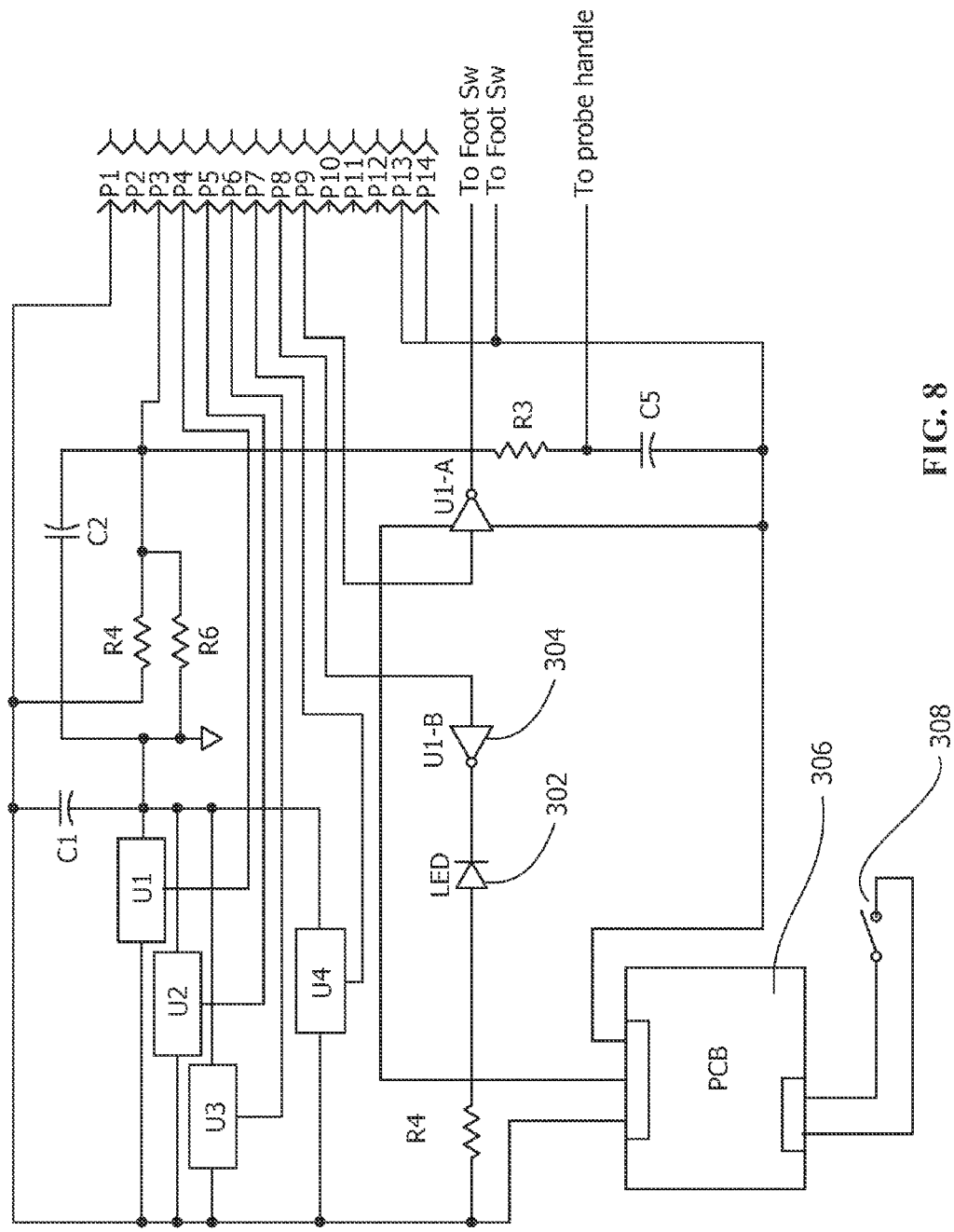
FIG. 8 is a schematic diagram of the foot pedal control circuit.

Referring next to FIG. 8, a schematic diagram of one embodiment of a foot pedal control circuit is shown. Four photo integrated circuits (IC) U1-U4 are connected in parallel between $V_{dd}$ and an R-C circuit R6, C2. Each IC U1-U4 is located on foot pedal 200 and is configured to detect a user's foot (or any article) when placed in proximity with the respective IC foot detectors U1-U4. Each of the IC outputs U1-U4 is connected to a 14-pin header strip in communication with a microprocessor, or other programmable controller or device. A green LED 302 is connected to Vdd through a resistor R4 on the input and a signal inverter 304 on the output. The LED provides a visual indication of the power status (ON or OFF) of the foot pedal. In one embodiment inverter 304 may be one logic gate of, e.g., a quad-Darlington switch Model No. L6220, such as manufactured by SGS Thompson Microelectronics. A second inverter 304 is another logic gate of the quad-Darlington switch, and is used to connect the microprocessor to a three-pin foot pedal connector. A local power supply 306 is connected to a foot pedal power switch 308 for providing power to the foot pedal 200. Additional resistors and capacitors R3, R4, C1 and C5 are included in the foot pedal circuit.

In another alternate embodiment ultrasonic scaler 54 and foot pedal controller 200 may be integrated into a dental chair. Integrating the ultrasonic scaler and foot pedal eliminates extra cords, frees up counter top space, and eliminates the need for a dedicated foot pedal control for the scaler only. When the clinician removes the scaler or any other handpiece from the chair's handpiece holder it becomes enabled and the rheostat on the dental chair can then control scaler activation.

To provide the pedal-tapping functionality for users that prefer an integrated ultrasonic scaler an additional air-logic module may be utilized. The air logic module is configured to monitor command signals from the dental chair rheostat. Most dental chairs use air logic to control dental handpiece operation. The rheostat provides air pressure to the handpiece in proportion to the extent that the rheostat is depressed by the clinician. The air logic module monitors air pressure from the rheostat using a pressure transducer or pressure switches. The pressure transducer approach monitors the rate of change in pressure and identifies a rapid increase and rapid decrease indicating that the chairs rheostat was quickly tapped initiating the tapping function software logic. The rapid impulse event, e.g., ramp-up and ramp-down, in pressure is distinguishable by the software from the pedal being pressed and held. To implement boost mode the pedal is depressed and maintained above a preset pressure limit, and a quick release of the pedal maintains scaler operation. To de-activate ultrasonic a simple tap on the foot pedal is applied. A pressure switch to close a circuit when air pressure develops a force sufficient to compresses a spring may be used also. The electronic controller may monitor the air switches for an event such as the switch transitioning from open to close and then returning to the open position in a short interval. The momentary switch closure can then initiate the pedal-tapping software logic. Beyond monitoring the rheostats' pressure lines a small module may be used to monitor the inclination of the foot pedal. The module may be attached to the top of the pedal. Pedal inclination and activity would be monitored with an accelerometer or tilt sensor providing information as to when the pedal has been tapped or fully depressed. A wireless or corded connection to the ultrasonic scaler module may be provided to control scaler operation.

An air logic module may also be employed to eliminate the need for an extra foot control in the dental operatory even when using a table top scaler. Table top scalers can provide more functionality than integrated systems, for example rinse and purge features. The air logic module may be arranged to fit in the dental chair handpiece holder. A standard dental hose connection may provide the air logic signals from the chair's rheostat. The air logic module may then be used to control the table top scaler via a wireless link. When the scaler is not in use it can be disabled at the unit or at the dental chair via a push button or toggle control that puts the scaling unit into a standby mode, thus ignoring rheostat activity.

It should be understood that the application is not limited to the details or methodology set forth in the following description or illustrated in the figures. It should also be understood that the phraseology and terminology employed herein is for the purpose of description only and should not be regarded as limiting.

While the exemplary embodiments illustrated in the figures and described herein are presently preferred, it should be understood that these embodiments are offered by way of example only. Accordingly, the present application is not limited to a particular embodiment, but extends to various modifications that nevertheless fall within the scope of the appended claims. The order or sequence of any processes or method steps may be varied or re-sequenced according to alternative embodiments.

The present application contemplates methods, systems and program products on any machine-readable media for accomplishing its operations. The embodiments of the present application may be implemented using an existing computer processors, or by a special purpose computer processor for an appropriate system, incorporated for this or another purpose or by a hardwired system.

It is important to note that the construction and arrangement of the foot pedal and foot pedal controller, as shown in the various exemplary embodiments is illustrative only. Although only a few embodiments have been described in detail in this disclosure, those who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present application. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the exemplary embodiments without departing from the scope of the present application.

As noted above, embodiments within the scope of the present application include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

It should be noted that although the figures herein may show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the application. Likewise, software implementations could be accomplished with standard programming techniques with rule based logic and other logic to accomplish the various connection steps, processing steps, comparison steps and decision steps.

What is claimed is:

1. A control system for controlling a dental instrument by a user's foot comprising:
    a foot pedal and a control circuit for communicating control signals from the foot pedal to the dental instrument, the foot pedal comprising at least two switches, the switches operable in response to a force applied to the foot pedal;
    the control circuit comprising control logic operable to:
        select a first operating mode for ultrasonic operation of the dental instrument in response to a sustained force applied to the foot pedal to move the foot pedal to a first level to actuate at least one switch on the foot pedal;
        select a second operating mode for ultrasonic operation of the dental instrument in response to a momentary force applied to the foot pedal to move the foot pedal to the first level; and
        transition ultrasonic operation of the dental instrument from the first operating mode, the second operating mode, an idle mode, and a boost mode in a predetermined sequence in response to applying the momentary force to the foot pedal.

2. The system of claim 1, wherein the control circuit is further operable to transition an operating mode of the dental instrument from the second operating mode to the first operating mode in response to applying sustained force to maintain the foot pedal at the first level.

3. The system of claim 2, wherein the control circuit is further operable to transition the operating mode of the dental instrument from the first operating mode to the second operating mode by applying a momentary force to the foot pedal.

4. The system of claim 1, wherein the control circuit is further operable to the operate in the boost mode of the dental instrument, the boost mode being an increased power level or frequency level relative to a normal ultrasonic mode.

5. The system of claim 1, wherein the control circuit is further operable to operate the dental instrument in the boost mode when the foot pedal is moved to the second level.

6. The system of claim 1, wherein the control circuit is further operable to:
    latch the dental instrument in the first operating mode in response to a momentary force applied to the foot pedal to;
    return the dental instrument to the idle mode from the first operating mode in response to a applying a subsequent momentary force of the foot pedal;
    transition the dental instrument into the boost mode when the foot pedal is moved to a second level by increasing the sustained force to actuate a second switch; and
    transition the dental instrument to the first operating mode in response to releasing the first switch and the second switch after the first switch and the second switch are held in a maintained normal mode.

7. The system of claim 1, wherein the control circuit is further operable to transition to a third operating mode, the third operating mode comprising alternating the dental instrument automatically between a jet polishing cycle and a prophylaxis rinse cycle.

* * * * *